United States Patent [19]

Baker et al.

[11] 4,191,046
[45] Mar. 4, 1980

[54] PERMEABILITY METERS

[75] Inventors: Richard R. Baker, Dibden Purlieu; Barry G. Bunn, Shirley, both of England

[73] Assignee: British-American Tobacco Company Limited, London, England

[21] Appl. No.: 918,708

[22] Filed: Jun. 26, 1978

[30] Foreign Application Priority Data

Jul. 1, 1977 [GB] United Kingdom ............ 27629/77

[51] Int. Cl.² ........................................ G01N 15/08
[52] U.S. Cl. ........................................ 73/38
[58] Field of Search ............................. 73/38, 37.7

[56] References Cited

U.S. PATENT DOCUMENTS

| | | | |
|---|---|---|---|
| 2,521,079 | 9/1950 | Morris | 73/38 |
| 2,861,451 | 11/1958 | Emmons | 73/38 |
| 3,524,341 | 8/1970 | Roy | 73/38 |
| 3,548,634 | 12/1970 | Roy | 73/38 |

*Primary Examiner*—Anthony V. Ciarlante
*Attorney, Agent, or Firm*—Kane, Dalsimer, Kane, Sullivan & Kurucz

[57] ABSTRACT

An instrument for measuring the air permeability of cigarette paper, including a paper-clamping head arranged to expose a fixed area of paper to a flow of pressurized air from an air pump. A manometer is arranged to measure the pressure differential across the paper and the gas flow is controllable by a control valve to enable a predetermined pressure differential to be maintained. The flow rate through the paper is measured by one of three flowmeters arranged in three parallel gas supply passages for measuring the flow rate in a low medium and high flow rate range respectively. The paper clamping head is such that the flow impedance downstream of the tapping point of the pressure transducer is negligible.

4 Claims, 5 Drawing Figures

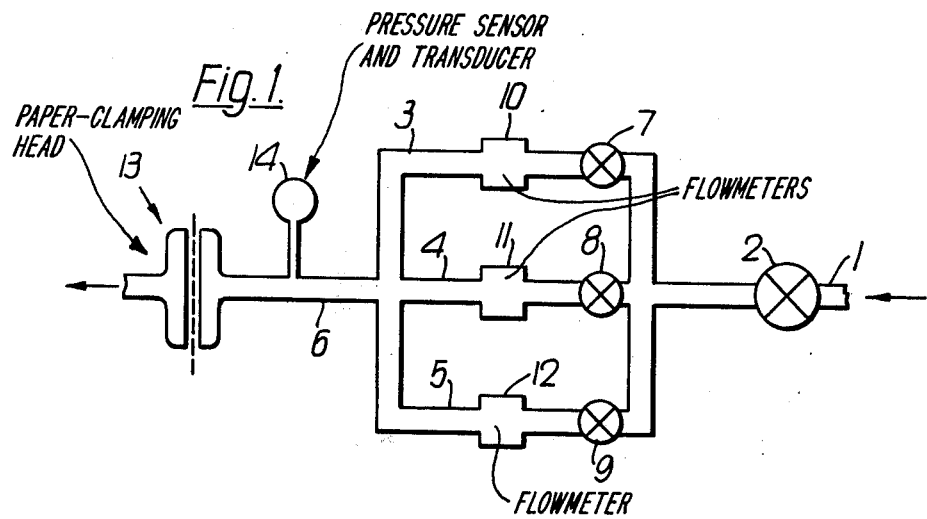
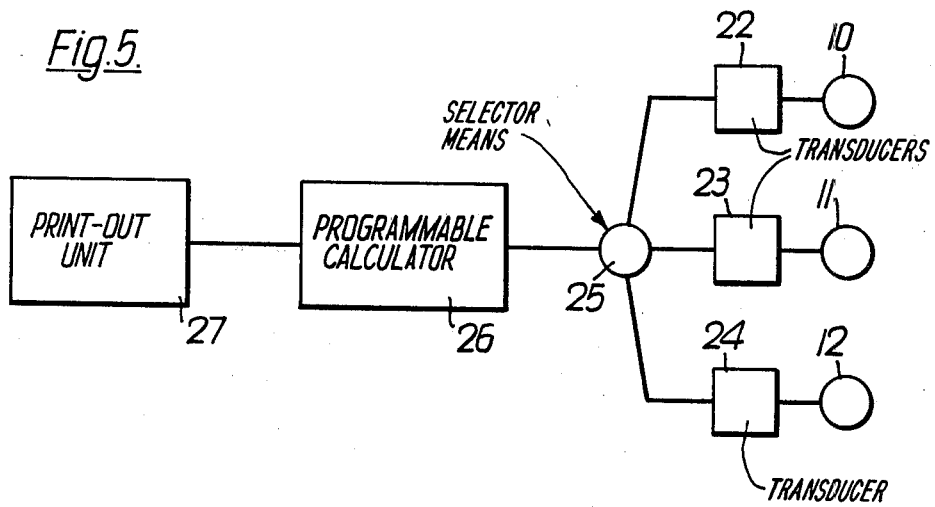

PERMEABILITY METERS

This invention relates to the measurement of the gas permeability of gas permeable materials, particularly but not exclusively the air permeability of cigarette paper.

The air permeability of paper may be expressed in Wiggins Teape (W.T.) Units, i.e. the rate of flow of air (expressed in cubic centimeters per minute) which is caused to flow through a 10 cm$^2$ zone of the paper under a pressure difference across that zone of the paper of 10 cm water.

There is known an instrument which is designed to give a direct reading of paper permeability in W.T. Units. This known instrument comprises a paper-clamping head arranged to expose a fixed area of paper to a flow of air there-through, pipework extending from the head to an air pump, an air control valve in said pipework, a manometer arranged to indicate the pressure differential across the area of paper, and three float flowmeters for measuring the rate of flow of air through the area of paper in a low, medium or high flowrate range respectively. In use of the known instrument, a portion of the paper, the permeability of which is to be measured, is clamped in the clamping head. With the air pump in operation a flow of air is caused to flow through the paper and then through the pipework to the pump, i.e. the flow is an induced flow. The flow rate of air is then adjusted by means of the air control valve so as to bring the indicated pressure differential across the paper to 10 cm water. The rate of flow of air (in cm$^3$/min.) is then read from the appropriate one of the three flowmeters.

The highest flowrate value which the high range flowmeter can measure is 3,000 cm$^3$/min. Thus if the area of paper exposed to the flow of air is 10 cm$^2$, the maximum permeability of which the instrument is capable of measuring is 3,000 W.T. The range of the instrument can, however, be extended by the use of a clamping head which exposes 2.5 cm$^2$ of the paper to the air flow. By this means, permeabilities of up to 12,000 W.T. nominal cab be measured. An attempt could, of course be made to further increase the range of this known instrument, but at above 12,000 W.T. the instrument becomes increasingly inaccurate. By way of example, whereas without paper in the clamping head and a flowrate of 3,000 cm$^3$/min., the manometer of the instrument shows a pressure drop of 2.8 cm water, this figure more than trebles to 9.4 cm if the flowrate is doubled. Thus, 12,000 W.T. nominal is the maximum practicable permeability value for this instrument. Even at permeabilities of below this value, correction factors have to be applied to the flow readings to compensate for flow impedance effects of the instrument.

In the known instrument, when there is a maximum flow rate reading of 3,000 cm$^3$/min with a pressure reading of 10 cm water, the actual pressure drop across the paper is only 7.2 cm, the remaining 2.8 cm being due to flow impedance effects of the instrument. The actual flow rate through the test area of the paper for an actual pressure difference across the paper of 10 cm water would be about 4,200 cm$^3$/min, i.e. 40% above the nominal value of 3,000 cm$^3$/min.

At the present time there is a tendency for use to be made of increasingly permeable cigarette papers, tipping papers and plugwrap papers. Plugwrap papers are now available having a permeability of 100,000 W.T., and can be made with a permeability of 300,000 W.T. There is thus required for, for example, quality control purposes, an instrument capable of the accurate measurement of permeabilities far greater than 12,000 W.T.

It is an object of the present invention to provide an instrument capable of measuring air permeability values much higher than the known instrument.

According to the present invention there is provided an instrument for measuring the gas permeability of a gas permeable material, including a clamping head arranged to clamp material between clamping faces thereof so that a portion of the material extends across the cross-section of gas-flow passageway means of the clamping head; gas supply means via which gas under pressure can be supplied to the passageway means of the clamping head, the gas supply means including a flowmeter and an adjustable control valve operable to control the flow rate of gas in said gas supply means; and pressure indicating means to indicate gas pressure differential across said portion of the material, the gas flow impedance of the instrument from the pressure tapping point of the pressure indicating means onwards being of such low value that in operation of the instrument the flow rate of gas, at a set reading of the pressure indicating means, can be determined by use of said flowmeter with substantially no need for a correction factor to be applied to the flow rate reading to compensate for instrument impedance effects.

In a preferred embodiment, for measuring the air permeability of paper, three passages are provided each adapted to measure a predetermined range of air flow. In this case, one of the passages may have a thermal flowmeter, the others having inductive rotary flowmeters. The pressure indicating means may comprise a pressure sensor and transducer located adjacent to but upstream of the clamping head.

The present invention will now be described by way of example, with reference to the accompanying diagrammatic drawings, in which:

FIG. 1 shows a sketch of an instrument for measuring the permeability of paper;

FIG. 5 shows in block diagram form a reading and/or recording arrangement for use with the instrument.

Figure 2:
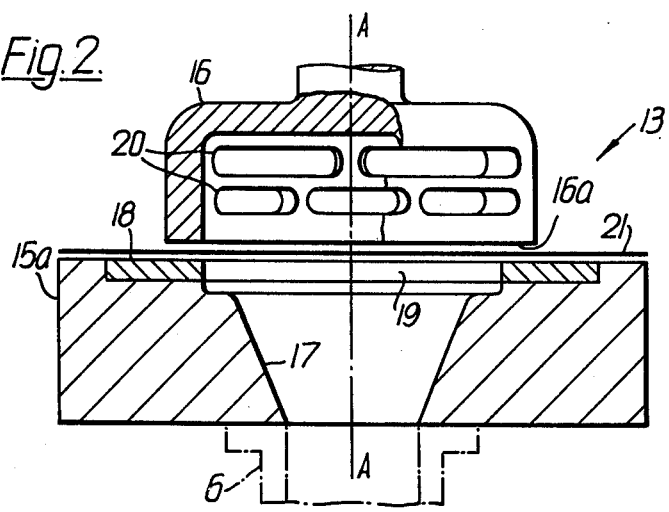
FIG. 2 shows, partly in section, an elevation of a paper-clamping head of the instrument shown in FIG. 1.

Referring to FIG. 1, the instrument there shown comprises an air inlet pipe 1, an air-control needle valve 2 fitted in the pipe 1 and including a disc type flow indicator, and three pipes 3–5 arranged in parallel so that each extends from the inlet pipe 1 to a pipe 6. Solenoid valve 7–9 are fitted in the pipes 3–5 respectively, so that by opening one of these valves 3–5 the pipe in which it is fitted provides an intercommunication between the pipe 1 and the pipe 6.

In the pipe 3 there is further fitted a thermal flowmeter 10 which is marketed by Hastings-Raydist under model designation AFSC/500. The flowmeter 10 is capable of measuring air flows in a range of 10 to 500 cm$^3$/min. Flowmeters 11 and 12 are similarly fitted in pipes 4 and 5 respectively. The flowmeters 11 and 12 are inductive rotary meters marketed by Liter Meter Limited under the name "Liter-Meter". Meter 11 measures air flow in a range of 500–5,000 cm$^3$/min., whereas the range of the meter 12 is 5,000–50,000 cm$^3$/min. Each of the meters provides a voltage reading from which the air flow value can be determined.

The pipe 6 extends to a paper-clamping head 13, and fitted in the pipe 6 is a pressure sensor and transducer 14. Electrical signals from the sensor/transducer 14 can be fed to digital indicating means (not shown) whereby a pressure reading in cm. water can be obtained.

Figure 3:
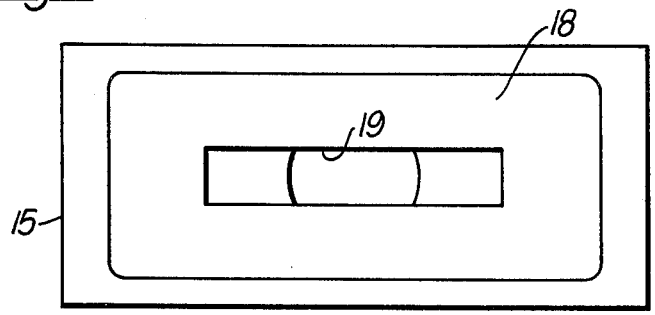
FIG. 3 shows a plan view of a lower member of the clamping head.
Figure 4:
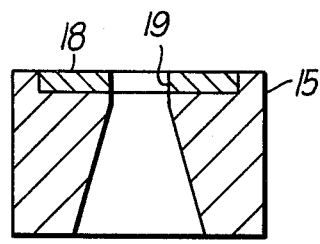
FIG. 4 shows a sectional view of the low member, taken on the line A—A of FIG. 2.

Referring now to FIGS. 2–4, the paper-clamping head 13 there shown comprises a stationary block 15 having a clamping face 15a and mounted thereabove a movable clamp 16 having a clamping face 16a. Extending upwardly through the block 15 is a passageway 17 which at its lower end is of circular cross section and at its upper end is of rectangular section (see FIG. 3). The upper rectangular opening of the passageway 17 has a transverse area of 10 cm$^2$. Set into the clamping face 15a of the block 15 is a sheet 18 of elastomeric material having a rectangular opening 19 therethrough, the sides of the opening 19 being aligned with corresponding sides of the upper opening of the passageway 17. As is indicated in broken lines in FIG. 2, the pipe 6 is in direct communication with the lower end of the passageway 17.

As can be observed from FIG. 2, the clamp 16 is of hollow construction and is opened downwardly in bell fashion. The inner surfaces of the side walls of the clamp 16 are aligned with corresponding sides of the opening 19 of the elastomeric sheet 18. A number of elongate air outlet holes 20 extend through each of an opposed pair of walls of the clamp 16.

When a sheet of paper 21, cigarette paper or cigarette plugwrap paper for example, has been inserted between the clamping faces of the block 15 and the clamp 16, the clamp 16 can be moved downwardly, by means of a mechanism not shown, so as to clamp the sheet of paper 21. The sheet of elastomeric material 18 acts as a seal. There is then presented to a flow of air passing upwardly into the passageway 17 from the pipe 6 a paper diaphragm which has an area of 10 cm$^2$, i.e. the area stipulated for the calculation of permeability in Wiggins Teape Units.

In operation of the instrument, after a sheet of paper has been clamped in the clamping head 13, and with the valves 2, 8 and 9 closed and the valve 7 open, air is admitted to the inlet pipe 1 from a source (not shown) of air under pressure. The needle valve 2 is then opened with a view to establishing a pressure reading from the sensor/transducer 14 of 10 cm water, i.e. that pressure differential stipulated for the calculation of paper permeability in Wiggins Teape Units. Should it not be possible to obtain a pressure reading of 10 cm water with an air flow rate within the range of the flowmeter 10 (this will be apparent from the coarse flow reading given by the disc indicator of the valve 2), valves 2 and 7 are closed and valve 8 is opened. An attempt is then made to obtain a pressure setting of 10 cm water with a flow rate of air within the range measurable by the flowmeter 11. If the paper is of very high permeability, it may be necessary to use the high range flowmeter 12. When a pressure setting of 10 cm water has been established the voltage reading of the flowmeter 10, 11 or 12 in use is indicative of the permeability of the paper as expressed in Wiggins Teape Units. It will thus be appreciated that the maximum permeability value measurable by the instrument is 50,000 W.T. Permeability values much in excess of this could however be measured by the simple expedient of employing a "Liter-Meter" flowmeter capable of measuring appropriately high flow rates.

Electrical signals from the flowmeters 10–12 can be fed to digital indicating means so that actual rate of flow readings in cm$^3$/min can be obtained. FIG. 5 shows an arrangement in which transducers 22, 23, 24 are each associated with a respective one of the flowmeters 10–12. A flow rate signal is fed from the flow meter in use, via the respective transducer, and a selector means 25 which selectively connects the appropriate flowmeter to a programable calculator 26. The calculator would be programmed with the equation of the curve representing the relationship between the actual air flow rate and the measured flowrate for each flowmeter. The true flow rate value derived in the calculator 26 is then fed to a read-out device 27, which may be a visual display, a print out unit, or means for entering the value on a punched or magnetic tape. Thus a direct reading of the actual air flow and hence the air permeability in W.T. Units is provided.

The design of the air passages in the instrument, especially in the clamping head and between the pressure measurement point and the clamping head, ensures that the impedance of the permeability measuring instrument is of a very low value so that permeabilities far exceeding 12,000 W.T. can be accurately measured.

For example, in our improved instrument when there is an air flowrate of 50,000 cm$^3$/min, with no paper in the clamping head, the pressure drop indicated is less than 0.01 cm water.

No correction factor is therefore required to be applied to the maximum flow rate reading of 50,000 cm$^3$/min. A very high degree of accuracy is maintained in use of the new instrument, with an appropriate flowmeter, to measure permeabilities much in excess of 50,000 W.T.

In the new instrument the pipe 6 has a cross-sectional internal area of 5 cm$^2$. The passageway 17 increases in cross-section to its upper opening of 10 cm$^2$ that is, twice the cross-sectional area of the pipe 6, and the air outlet holes 20 in the clamp 16 have a total cross-sectional area of 6.2 cm$^2$ that is, approximately 24% greater than the cross-sectional area of the pipe 6. Dimensions such as this result in a very low flow impedance. Thus a reading of permeability with a high degree of accuracy is possible.

We claim:

1. An instrument for measuring the gas permeability of a gas permeable paper of high permeability, the instrument including a clamping head having clamping faces and gas-flow passageway means and arranged to clamp paper between said clamping faces so that a portion of the paper extends across the cross-section of said gas-flow passageway means; gas supply means via which gas under pressure can be supplied to the passageway means of the clamping head, the gas supply means including a flow meter and an adjustable control valve to control the flow rate of gas in said supply means; and pressure indicating means including a pressure sensor responsive to gas pressure located adjacent to but upstream of the clamping faces to indicate gas pressure differential across said portion of the paper, the passageway between the clamping head and the pressure sensor being dimensioned to provide minimal impedance so that the gas flow impedance of the instrument from the pressure sensor onwards is less than 0.1% of the set pressure, that is 0.01 cm water at 50,000 cubic meters per minute gas flow so that, in operation of the instrument, the flow rate of gas, at a set reading of the pressure indicating means, can be determined by use of said flow meter with substantially no need for a correction factor to be applied to the flow rate reading to compensate for instrument impedance effects.

2. An instrument as claimed in claim 1 wherein a plurality of passages are provided in the gas supply means, each including a flow meter adapted to measure a predetermined range of gas-flow.

3. An instrument as claimed in claim 2 wherein one of the passages has a thermal flow meter, the remainder having inductive rotary flow meters.

4. An invention as claimed in claim 1 wherein the cross-sectional area of the passageway means at the upstream end of the clamping head is approximately half that of the passageway means at the clamping faces.

* * * * *

UNITED STATES PATENT AND TRADEMARK OFFICE
CERTIFICATE OF CORRECTION

PATENT NO. : 4,191,046
DATED : March 4, 1980
INVENTOR(S) : Richard R. Baker & Barry G. Bunn It is certified that error appears in the above—identified patent and that said Letters Patent is hereby corrected as shown below:

At col. 4, line 68; "meters" should be --centimeters--.

Signed and Sealed this

Sixth Day of January 1981

[SEAL]

Attest:

SIDNEY A. DIAMOND

Attesting Officer

Commissioner of Patents and Trademarks